United States Patent [19]

Nonobe et al.

[11] Patent Number: 5,728,539
[45] Date of Patent: Mar. 17, 1998

[54] ENZYMATIC METHODS FOR MEASUREMENT OF MINUTE AMOUNTS OF COPPER

[75] Inventors: Masatsugu Nonobe, Hyogo-ken; Hozumi Hamasaki; Tsuyoshi Fujita, both of Osaka-fu, all of Japan

[73] Assignee: Oriental Yeast Co., Ltd., Tokyo, Japan

[21] Appl. No.: 563,257

[22] Filed: Nov. 28, 1995

Related U.S. Application Data

[63] Continuation of Ser. No. 177,987, Jan. 6, 1994, abandoned.

[30] Foreign Application Priority Data

Jan. 13, 1993 [JP] Japan .................................. 5-019397

[51] Int. Cl.$^6$ .............................. C12Q 1/54; G01N 33/20
[52] U.S. Cl. .............................. 435/14; 435/4; 435/190; 436/73; 436/74; 436/80
[58] Field of Search .............................. 435/14, 4, 190; 436/73, 74, 80

[56] References Cited

U.S. PATENT DOCUMENTS

| | | | |
|---|---|---|---|
| 4,335,213 | 6/1982 | Terada et al. | 435/190 |
| 5,149,646 | 9/1992 | Crane et al. | 435/190 |

FOREIGN PATENT DOCUMENTS

| | | |
|---|---|---|
| 0555046 | 8/1993 | European Pat. Off. |
| 63-214199 | 9/1988 | Japan |

OTHER PUBLICATIONS

Sasaki, *Biochemical Tests Using Enzymes* Media Circle, vol. 32, No. 5, pp. 209–217, May 1987.
Aisaka et al, Reactivation of Gibberella Apogalactose–oxidase by Cooper, *Agri. Biol. Chem.*, vol. 48, No. 8, pp. 2157–2158, 1984.
Kosman et al, *Biochemistry*, vol. 19, No. 7, pp. 1304–1308, 1980.
Satoh et al, Amperometric Biosensing of Cooper (II) Ions with an Immobilized Apoenzyme Reactor, *Sensors and Actuators B*, vol. B1, pp. 499–503, 1990.
Kosman et al., The Molecular Properties of the Copper Enzyme Galactose Oxidase, Archives of Biochemistry and Biophysics, vol. 165, No. 2, pp. 456–467, 1974.
Kosman et al, Role of Tryptophan in the Spectral and Catalytic Properties of the Copper Enzyme, Galactose Oxidase, Biochemistry, vol. 16, No. 8, pp. 1597–1601, Apr. 19, 1977.
Amaral et al, Galactose Oxidase of Polyporus circinatus, Methods of Enzymology, vol. 9, pp. 87–92.
Whittaker et al, A Tyrosine–derived Free Radical in Apogalactose Oxidase, The Journal of Biological Chemistry, vol. 265, No. 17, pp. 9610–9613, Jun. 15, 1990.
Yasmineh et al, Determination of Serum Catalase Qctivity on a Centrifugal analyzer by an NADP/NADPH Coupled Enzyme Reaction System, Clinical Biochemistry, vol. 25, No. 1, pp. 21–27, Feb. 1992.
Matsumoto et al, 3–(p–Hydroxyphenyl)propionic Acid as a New Fluorogenic Reagent for Amine Oxidase Assays, Analytical Biochemistry, vol. 138, No. 1, pp. 133–136, Apr. 1984.
Walusimbi–Kisitu et al, Fluorometric assay for rat liver peroixisomal fatty acyl–coenzyme A oxidase activity, Journal of Lipid Research, vol 24, No. 8, pp. 1077–1084, 1983.
Cederbaum et al, Inhibition of the Peroxidatic Activity of Catalase Towards Alcohols by the Aldehyde Dehydrogenase Inhibitor Cyanamide, Toxicology Letters, vol. 29, pp. 107–114, 1985.

*Primary Examiner*—Cecilia J. Tsang
*Assistant Examiner*—Abdel A. Mohamed
*Attorney, Agent, or Firm*—Browdy and Neimark

[57] ABSTRACT

An accurate and effective measurement of copper in subject samples is rendered possible even for minute amounts of copper, by converting copper-bonded hologalactose oxidase to the apo-form by liberation of the copper, and measuring the copper of the sample in a reaction system containing the apogalactose oxidase.

8 Claims, 2 Drawing Sheets

5,728,539

ENZYMATIC METHODS FOR MEASUREMENT OF MINUTE AMOUNTS OF COPPER

This application is a continuation of application Ser. No. 08/177,987, filed Jan. 6, 1994 now abandoned.

FIELD OF THE INVENTION

The present invention relates to a method for the measurement of copper, and more specifically, it relates to a highly sensitive enzymatic measurement method for the measurement of copper in specimens, whereby hologalactose oxidase is treated to liberate copper bound to the enzyme, producing apogalactose oxidase (EC 1.1.3.9) which expresses no activity unless converted to the holo-form by the addition of copper. The copper contained in the specimen is used to convert the apogalactose oxidase into the active form, and the amount of the converted apogalactose oxidase is then measured.

DESCRIPTION OF THE PRIOR ART AND SUBJECT MATTER

Copper is an essential trace element which is widely distributed throughout the body, and which contributes to important reactions in the body, mainly as a cofactor bound to metalloproteins. Representative copper-bound metalloproteins include ceruloplasmin which contributes to iron oxidation and copper transport, cytochrome which contributes to respiration, lysyl oxidase and amine oxidase which contribute to the cross-linking of collagen, etc., tyrosinase which contributes to melanin metabolism, dopamine-β-hydroxydase which contributes to epinephrine synthesis, superoxide dismutase which contributes to superoxide radical metabolism, etc.

In the field of clinical analysis, blood serum, plasma or urine are generally used as the specimens for the measurement of copper, and diagnosis of metabolic disorders and diseases are made thereby. In the blood, the majority of copper is bound to ceruloplasmin which, as mentioned above, plays a physiological role, such as in promoting the binding of iron to transferrin, and in the transport of copper and the maintenance thereof in the blood.

Copper is present in the blood only in minute amounts, with a normal value of 12.9–21.1 μmol/l for males, and 16.2–25.0 μmol/l for females. In routine medical care, a greater problem occurs when a low value, rather than a high value, of serum copper is shown, such as represented Wilson's disease and Kinky Hair disease, and therefore a measurement method has been desired which can accurately measure amounts of copper even more minute than the normal values.

Methods generally used for copper measurement include the atomic absorption method and the chelate colorimetric method, etc. However, the atomic absorption method not only requires expensive special equipment, but in the flame atomization method, despite the large amount of antibody needed, the sensitivity is poor for serum and plasma specimens. In the graphite reactor atomization method, the sensitivity is too high, requiring dilution of the specimen, and thus raising the possibility of contamination due to pollution from the containers. The chelate colorimetric method is widely used in clinical examinations. The chelate colorimetric method is vastly superior to the atomic absorption method in that a commonly used autoanalyzer which is found in any clinical examination room may be applied, but since copper is found only in minute amounts in serum and plasma specimens as mentioned above, this method is often unsatisfactory from the point of view of sensitivity and accuracy.

DETAILED DESCRIPTION OF THE INVENTION

Figure 1:
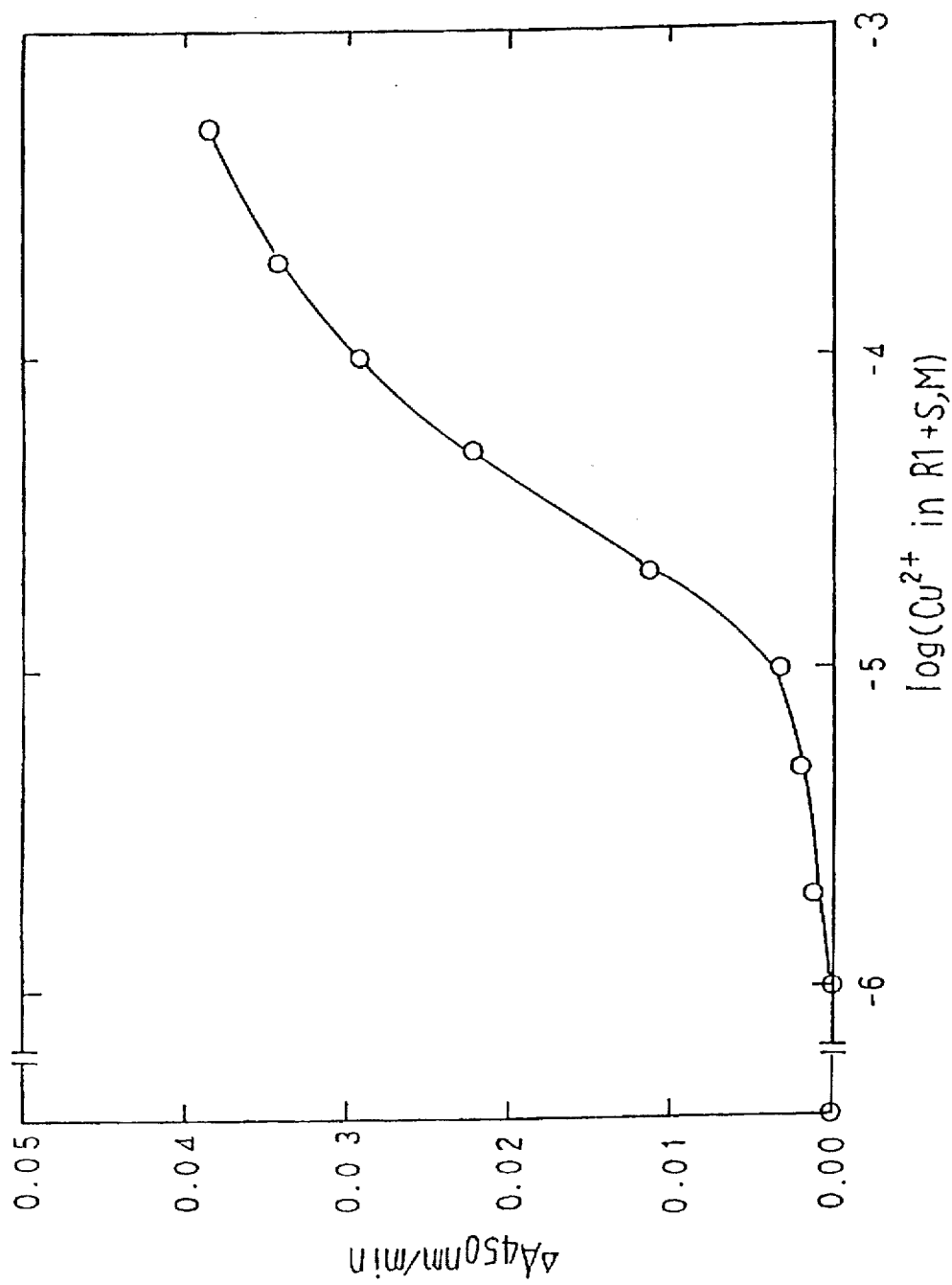
FIG. 1 is a graph showing the km values of apogalactose oxidase for copper, measured according to the method described in Example 2.

The present invention provides a possibility for the development of a novel highly sensitive analysis system for serum copper, which overcomes all of the above mentioned disadvantages of the prior art, by making possible an accurate, convenient and quick measurement of copper in the blood, and particularly in the serum, without requiring special skill, while also allowing for automation and treatment of multiple specimens.

The present invention was conceived in order to achieve the above mentioned object, and we, the present inventors, with the object of measuring minute amounts of copper in a quick and accurate manner, have carried out detailed research regarding the relationship between copper and various enzyme activities. As a result, we have realized that the activity of galactose oxidase, and specifically apogalactose oxidase, which is produced advantageously by treating copper-bound hologalactose oxidase so as to liberate the copper bound to the enzyme, and which expresses no activity unless converted to the holo-form by the addition of copper, changes according to the difference in the concentration of copper added from a specimen, in the range which is required for the measurement of minute amounts of copper we have further confirmed that measurement of minute amounts of copper may be made by measuring this change, and thus the present invention has been completed.

According to the present invention, a plurality of responses may be obtained for each copper atom even in the case of minute amounts of copper, due to the amplifying effect of galactose oxidase. Thus, the method has the advantage of providing a high sensitivity which is absolutely unobtainable according to the conventional methods.

It is known that galactose oxidase is a protein enzyme to which copper is bound (Archives of Biochemistry and Biophysics 165, 456–467, 1974; Biochemistry, Vol. 16, No. 8, 1597–1601, 1977, etc.). Further, the method for the preparation of apogalactose oxidase (Method. in Enzymol., Vol. 9, 87–92) and the method for the conversion of apogalactose oxidase into the holo-form (J. Biol. Chem., Vol. 265, No. 17, 9610–9613, 1990), etc. are publicly known techniques. In addition, a report has also been made regarding an idea for the application of galactose oxidase in clinical examinations (Media Circle, Vol. 32, No. 5, 209–217, 1987). Nevertheless, until presently there has been absolutely no example of copper measurement which actually deals with minute amounts of copper such as are found in blood serum and plasma, as mentioned above.

The method according to the present invention is one in which non-copper-bound apogalactose oxidase is first prepared, then a minute amount of copper is allowed to bind to this non-active apogalactose oxidase, and the copper content is detected in the form of the level of the oxidase activity which depends on the amount of the active form formed, hologalactose oxidase. Thus, a highly repeatable and sensitive method of measurement of copper is made possible.

The galactose oxidase which may be used according to the present invention is preferably a commercially available galactose oxidase derived from mold (*Dactylium dentroides*), but any galactose oxidase may be applied to the method according to the present invention so long as copper is bound to the galactose oxidase and may be relatively readily liberated therefrom, and providing its activity may be restored by the addition of copper thereto.

The purchased enzyme is already bound with copper, and therefore must be converted to the apo-form before being applied to the method according to the present invention.

The method of preparing the apogalactose oxidase may be a pH treatment or a treatment with a chelating agent. However, since pH treatment has the possibility of causing a lowering of the activity by deactivation, treatment with a chelating agent is preferred. The chelating agent to be used is a reagent which reduces to a minimum the residual activity of the treated apogalactose oxidase. That is, it is preferable to use one with a large chelate stability constant with respect to copper. For use in the method according to the present invention, the enzyme is treated with EDTA (ethylenediamine tetraacetic acid), CyDTA (trans 1,2-cyclohexanediamine-N,N,N",N"-tetraacetic acid), DTPA (diethyltriamine pentaacetic acid), TTHA (triethyltetraamine hexaacetic acid), EDTPO (ethylenediamine tetrakis-methylenephosphonic acid), o-phenanthroline or dithiopyrocarbonate, etc. under mild conditions and allowed to stand for a determined period of time, after which the chelating agent is completely removed.

The galactose oxidase activity of the active form resulting from holo-formation by the copper contained in the sample may be detected by measuring the amount of dissolved oxygen consumed, by measuring the reduced amount of galactose, or by measuring the amount of hydrogen peroxide produced. As it is common in clinical examinations to use the method whereby the amount of hydrogen peroxide is measured, this method is preferred, and examples thereof are given below.

First is a method using peroxidase and a chromogen, in which, for example; o-dianisidine or phenol-4-aminoantipyrine is used with peroxidase and the coloration of the condensate produced by hydrogen peroxide is measured. Recently, further improved chromogens have been developed.

Second is the glutathione peroxidase method (Japanese Patent Application SHO 62-47725(JP-A 63-214199), owned by Oriental Yeast Co., Ltd.: "Enzyme Assays of Biological Substances") which corresponds to EP-A 0386237. This is an excellent method, since the presence of large amounts of the reducing agent glutathione in the reagent reduces the influence of reducing substances in the specimen, and since glutathione reductase is coupled therewith for detection of the reduced rate of NADPH, it is also possible to eliminate the influence of not only reducing substances but also bilirubin.

Third is the catalase method (Clic. Biochem., Vol. 25, No. 1, 21–27, 1992; Toxicol. Lett., Vol. 29, 107–114, 1985), in which peroxidase produced by using catalase is reacted with ethanol to produce acetaldehyde. The acetaldehyde is oxidized with acetaldehyde dehydrogenase and NAD(P), and measurement is made by detection of the resulting NAD(P)H. This measurement method uses an absorption wavelength of 340 nm, and therefore, as in the glutathione peroxidase method, this measurement method theoretically receives the influence of interfering substances less than in the method using peroxidase and a chromogen.

A slightly unorthodox measurement method is the fluorescence, analysis method (Anal. Biochem., Vol. 138, 133–136, 1984; J. Lipid. Res., Vol. 24, No. 8, 1077–1084, 1983).

Any of these methods may be applied to the method according to the present invention.

A more concrete description of the method according to the present invention will now be provided with reference to the Examples, but it is by no means restricted thereby.

EXAMPLE 1

Preparation of apogalactose oxidase

To galactose oxidase (5,000 units) produced by Boehringer Co. was added 80 ml of a 20 mM PIPES-NaOH buffer containing 1 mM diethyl dithiocarbamate, pH 7.0, and the reaction was conducted at 25° C. for 10 minutes. The mixture was then desalted with Sephadex G-25 to obtain 5 ml of a 320 u/ml enzyme solution.

EXAMPLE 2

Measurement of km value for copper

Reagents R1 and R2 were prepared with the compositions listed in Table 1 below.

TABLE 1

| Reagent R1: | 48 mM PIPES-NaOH, pH 7.2 |
| | 0.07 u/ml apogalactose oxidase |
| Reagent R2: | 95 mM sodium phosphate, pH 7.0 |
| | 0.5% galactose |
| | 0.05 mg/ml peroxidase (product of Boehringer Co.) |
| | 0.05 mg/ml o-dianisidine |

Measurement method

To 90 μl of R1 was added 10 μl of a copper solution, and the mixture was pre-incubated at 37° C. for 5 minutes. Three hundred μl of R2 was added thereto, the mixture was allowed to stand at the same temperature for 2 minutes, and the change in the absorbance at 450 nm was measured for 1 minute thereafter. A graph was drawn with the copper concentration upon mixing of R1 and the copper solution plotted on the horizontal axis, and the change in absorbance plotted on the vertical axis. The results are shown in FIG. 1.

Results

As shown in FIG. 1, absolutely no enzyme activity was exhibited with a final copper concentration of 10 μM or lower, showing complete conversion to apogalactose oxidase by the treatment in Example 1. Furthermore, the km value obtained for the copper under these conditions was 43.9 μM, showing that the enzyme was suitable for the measurement of copper concentration in the serum and plasma.

EXAMPLE 3

Assay curve

Reagents R1 and R2 were prepared with the compositions listed in Table 2 below.

TABLE 2

| Reagent R1: | 100 mM sodium acetate, pH 5.0 5 u/ml apogalactose oxidase |
|---|---|
| Reagent R2: | Same reagent as in Example 2 |
| Sample S: | 0–50 μM of copper solution |

Measurement method

The measurement was made under the same conditions as in Example 2. A graph was drawn with the copper concentration of the sample plotted on the horizontal axis, and the change in absorption plotted on the vertical axis, subtracting the sample blank. The results are shown in FIG. 2.

Results

Figure 2:
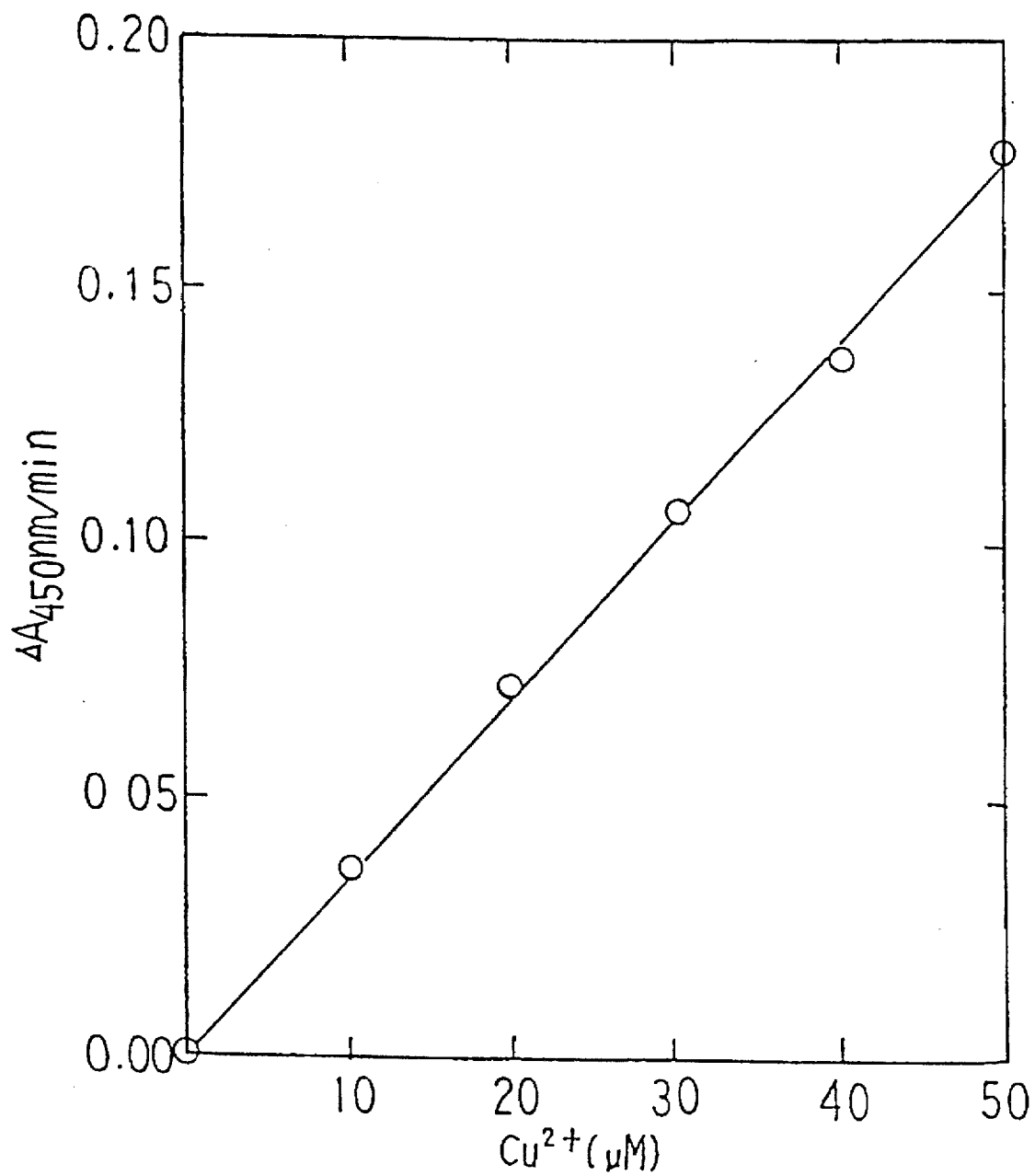
FIG. 2 shows an assay curve for copper, measured according to the method described in Example 3.

As shown in FIG. 2, an assay curve was obtained with the 0–50 μM copper solutions. This shows that a highly sensitive measurement may be made even for minute amounts of copper in the serum and plasma.

Effect of the Invention

Copper-bonded hologalactose oxidase is converted to the apo-form by liberation of the copper, and copper of a sample may be measured in a reaction system containing the formed apogalactose oxidase.

What is claimed is:

1. An assay method for the measurement of copper, comprising the steps of:

preparing apogalactose oxidase at a high concentration;

reacting a sample containing copper in the concentration range between 0–50 μM with said apogalactose oxidase in a buffer, which does not interfere with the binding of copper to said apogalactose oxidase, to reactivate said apogalactose oxidase into hologalactose oxidase; and determining the amount of copper in said sample by either absorbance or fluorescence measurement.

2. An assay method according to claim 1, wherein said sample is a body fluid selected from blood serum, plasma, and urine, and having a copper concentration in the range of about 0–50 μM.

3. An assay method according to claim 1, wherein said step of preparing apogalactose oxidase comprises pretreating hologalactose oxidase to liberate copper ions bound to the hologalactose oxidase and to convert the hologalactose oxidase to apogalactose oxidase.

4. An assay method according to claim 3, wherein said step of pretreating hologalactose oxidase is a pH treatment.

5. An assay method according to claim 3, wherein said step of pretreating hologalactose oxidase comprises:

treating with a chelating agent; and removing said chelating agent.

6. An assay method according to claim 5, wherein said chelating agent is selected from the group consisting of ethylenediamine tetraacetic acid, trans 1,2-cyclohexanediamine-N,N,N",N"-tetraacetic acid, diethyltriamine pentaacetic acid, triethyltetraamine hexaacetic acid, ethylene diamine tetrakis-methylene phosphoric acid, o-phenanthroline, dithiopyrocarbonate, and diethyl dithiocarbamate.

7. An assay kit for the measurement of copper according to claim 1, comprising:

a first assay reagent containing galactose oxidase at a high concentration; and a second assay reagent containing a buffer which does not interfere with the binding of copper to apogalactose oxidase.

8. An assay kit for measurement of copper according to claim 7, wherein said galactose oxidase is apogalactose oxidase.

* * * * *